United States Patent [19]

Wu

[11] Patent Number: 5,118,825
[45] Date of Patent: Jun. 2, 1992

[54] RUTHENIUM PHOSPHINE COMPLEX

[75] Inventor: Tse-Chong Wu, Baton Rouge, La.

[73] Assignee: Ethyl Corporation, Richmond, Va.

[21] Appl. No.: 624,575

[22] Filed: Dec. 10, 1990

[51] Int. Cl.$^5$ .............................................. C07F 15/00
[52] U.S. Cl. ...................................... 556/21; 556/136
[58] Field of Search ...................... 556/18, 23, 21, 13, 556/136; 568/8, 10

[56] References Cited

U.S. PATENT DOCUMENTS

| | | | |
|---|---|---|---|
| 4,691,037 | 9/1987 | Yoshikawa et al. | 556/18 |
| 4,739,084 | 4/1988 | Takaya et al. | 556/21 |
| 4,739,085 | 4/1988 | Takaya et al. | 556/21 |
| 4,766,227 | 8/1988 | Sayo et al. | 556/21 |

OTHER PUBLICATIONS

ApSimon et al., Tetrahedron (1986) 42, 5157.
Inoue et al., Chem. Lett., (1985), 1007.
Bosnich et al., JACS 103, 2273 (1981).
Noyori et al., Mod. Synthetic Methods (1989) 5, 115.
Wilson et al., Syn Lett (1990), 199.

Primary Examiner—Jose G. Dees
Assistant Examiner—Joseph Conrad, III
Attorney, Agent, or Firm—Richard J. Hammond

[57] ABSTRACT

A ruthenium phosphine complex having catalytic, hydrogenation activity is disclosed. The catalyst as the formula

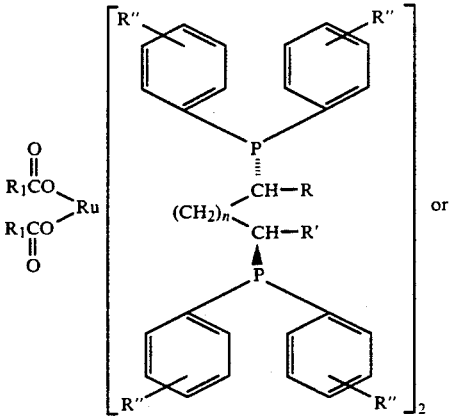

or

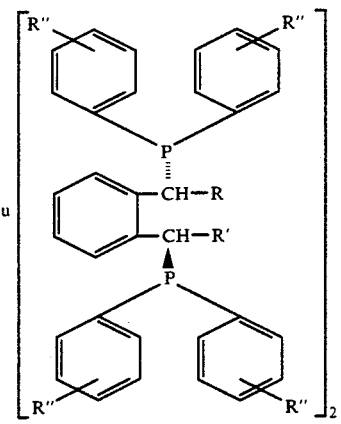

wherein R and R' are the same or different and are $C_1$ to $C_6$ linear or branched alkyl; R" is hydrogen or $C_1$ to $C_6$ linear or branched alkyl; $R_1$ is $C_1$ to $C_6$ linear or branched alkyl; and n is an integer from 1 to 6.

The phosphine complex is particularly useful in the asymmetric hydrogenation of unsaturated carboxylic acids or alkyl esters thereof.

8 Claims, No Drawings

RUTHENIUM PHOSPHINE COMPLEX

FIELD OF INVENTION

The present invention relates to a ruthenium phosphine complex and the use of that complex to reduce certain organic compounds. More particularly, this invention is concerned with a ruthenium phosphine complex which is used as a catalyst in various olefinic and asymmetric olefinic reductions.

BACKGROUND OF THE INVENTION

Enantioselective catalysis using chiral metal complexes provides one of the most general and flexible methods for achieving asymmetric organic reactions. Metallic elements possess a variety of catalytic activities, and permutations of organic ligands or other auxiliary groups directing the steric course of the reaction are practically unlimited. Efficient ligands must be endowed with, for example, suitable functionality, an appropriate element of symmetry, substituents capable of differentiating space either electronically or sterically, and skeletal rigidity or flexibility.

Among the asymmetric organic reactions catalyzed by chiral transition metal complexes, asymmetric hydrogenation has been one of the best studied, due in large part to the fact that it is the basis for the first commercialized catalytic asymmetric process. See, for example, ApSimon, et al., *Tetrahedron*, 1986, 42, 5157.

Some of the more interesting of the asymmetric hydrogenation catalysts are those derived from BINAP [2,2'-bis(diphenylphosphino)-1,1'-binaphthyl]. See, for example, U.S. Pat. Nos. 4,691,037; 4,739,084; 4,739,085; and 4,766,227. Unlike the more classical models of chiral (asymmetric) molecules, chirality in the case of the BINAP compounds arises from the restricted rotation about the single bond joining the naphthalene rings. Because of such restricted rotation, perpendicular disymmetric planes result. Isomers arising from this type of asymmetry are termed atropisomers.

Cationic rhodium-BINAP complexes have been shown to catalyze the isomerization of allylamines to chiral enamines in 94-96% ee. Also, hydrogenations of geraniol and nerol (bis-unsaturated alcohols) using rhodium-BINAP complexes produce products in about 50% ee's. The synthesis of BINAP derivatives bearing groups other than phenyl on phosphorus such as paramethylphenyl and cyclohexyl have also been prepared. Inoue, et al., *Chem. Lett.*, 1985, 1007. Other rhodium complexes have been prepared. See, for example, Bosnich, et al., *J. Am. Chem. Soc.*, 103, 2273 (1981).

The BINAP ruthenium complexes have been used to catalyze a variety of asymmetric hydrogenations including the reduction of enamides, alkyl and aryl-substituted acrylic acids, homoallylic alcohols and functionalized ketones. See Noyori, et al., *Modern Synthetic Methods*, 1989, 5, 115, incorporated herein by reference. While these complexes are effective in facilitating the asymmetric reduction of the above compounds, they are difficult to prepare and expensive to produce.

DESCRIPTION OF THE PREFERRED EMBODIMENTS

The compounds of the present invention are phosphine ruthenium complexes having the formula

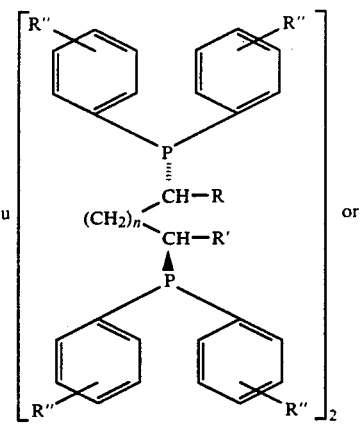 or

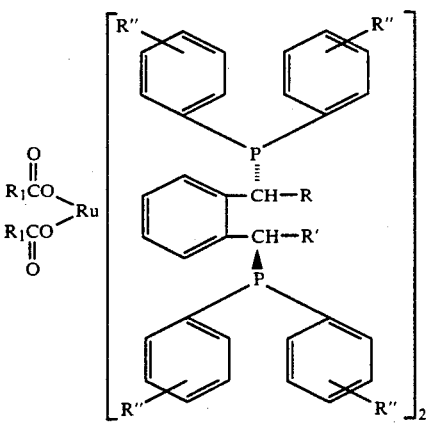

where R and R' are the same or different and are $C_1$ to $C_6$ or branched alkyl; R" is hydrogen or $C_1$ to $C_6$ linear or branched alkyl; $R_1$ is $C_1$ to $C_6$ linear or branched alkyl; and n is an integer from 1 to 6. (The term "alkyl" as sometimes used herein refers to $C_1$ to $C_6$ linear or branched alkyl).

In the compounds of the present invention, it is preferred that R and R' are the same or different and are $C_1$ to $C_3$ linear or branched alkyl, i.e., methyl, ethyl, n-propyl or isopropyl. In such preferred compounds, R" is methyl, ethyl, n-propyl or isopropyl, and R is also methyl, ethyl, n-propyl or isopropyl.

Most preferably, in the compounds of the present invention, $R_1$ is methyl, R and R' are the same and are methyl, R" is hydrogen, and n is 2. Of these most preferred compounds, it is particularly preferred that the compounds are optically active and are 2R,5R-bis(diphenylphosphino)hexane ruthenium diacetate or [1-(1R-ethyl)-2-(1R-ethyl)-bis(diphenylphosphino)]benzene ruthenium diacetate.

The ruthenium complexes of the present invention are readily prepared by first reacting dichloro-(1,5-cyclooctadiene)-ruthenium polymer with

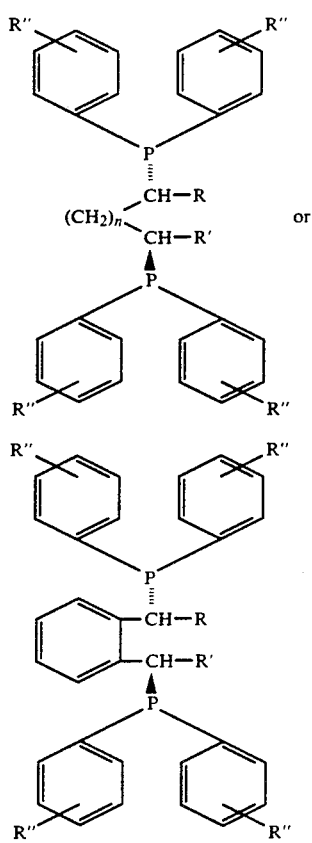

in the presence of a tertiary amine in a solvent.

Examples of the tertiary amine which can be used in the reaction include triethylamine, tri-n-butylamine, tri-n-octylamine, N-methyl piperidine, N-methyl pyrrolidine, N-methyl morpholine, pyridine, dimethylaniline and tetramethyl ethylenediamine.

The ruthenium complex formed from this initial reaction is then further treated with the alkali metal salt of an aliphatic carboxylic acid. Typically the salt is from $C_1$ to $C_6$ linear or branched aliphatic carboxylic acid, preferably the acetate, proprionate or butyrate salt.

In particular, 1 mole of dichloro-(1,5-cyclooctadiene)-ruthenium polymer is treated with a stoichiometric amount of the bis(diphenylphosphino) compound (with heating) and about a 10 fold excess of the tertiary amine. The resulting product is then treated with an excess of one of the alkali metal carboxylates indicated above. After further heating, the compounds of the present invention are isolated in good yield.

The ruthenium complexes prepared as indicated above are useful as catalysts for the hydrogenation of a variety of olefinic compounds. The compounds particularly susceptible to such procedures are those compounds of the formula

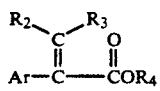

where $R_2$ and $R_3$ are the same or different and are hydrogen or $C_1$ to $C_6$ linear or branched alkyl; $R_4$ is hydrogen or $C_1$ to $C_6$ linear or branched alkyl; and Ar is phenyl or naphthyl unsubstituted or substituted with one or more $C_1$ to $C_6$ linear or branched alkyl or $C_1$ to $C_6$ linear or branched alkoxy, halo, amino or carboxylic acid or alkyl ester thereof.

In the above olefin compounds, it is preferred that $R_2$ and $R_3$ are the same or different and are hydrogen, methyl, ethyl or isopropyl, and $R_4$ is hydrogen, methyl or ethyl. Most preferably, $R_2$, $R_3$ and $R_4$ are hydrogen.

For the above preferred and most preferred compounds, it is preferred that Ar is phenyl or naphthyl unsubstituted or substituted with $C_1$ to $C_6$ linear or branched alkyl or $C_1$ to $C_6$ linear or branched alkoxy. Most preferably, Ar is phenyl substituted with isobutyl or naphthyl substituted with methoxy.

The reductions (hydrogenations) of the olefinic materials with the ruthenium complexes of the present invention are typically carried out in a suitable inert solvent under a hydrogen pressure of up to about 2000 psi and at a temperature from about 20° C. to about 75° C. However, temperatures and pressures are only critical in that the rate of hydrogen uptake, i.e., rate of reduction, is affected by these parameters (higher pressures and temperatures will generally result in faster reductions).

The present invention is described in greater detail by reference to the accompanying examples. However, these examples are not to be regarded as limiting in any way.

EXAMPLES

EXAMPLE 1 a) Preparation of 2S,5S-Hexanediol 2,5-Bismethanesulfonate

This compound was prepared from 2,5-hexanedione by the procedure of Wilson and Pasternak. Reference: Wilson, S. R.; Pasternak, A. SynLett 1990, 199.

b) Preparation of 2R,5R-Bis(diphenylphosphino)hexane

A solution of diphenylphosphine (1.30 g, 6.98 mmol) in freshly distilled THF (10 mL) was slowly treated with butyllithium (2.5M in hexane, 2.8 mL, 7.0 mmol) via a syringe at 0° C. under $N_2$ atmosphere. After the addition of butyllithium solution, the reaction mixture was allowed to warm to room temperature for 30 min. The reaction mixture was cooled to −78° C., and 2S,5S-hexanediol 2,5-bismethanesulfonate (0.92 g, 3.35 mmol) in THF (11 mL, including 1 mL of washing) was added dropwise at −78° C. This orange solution was gradually warmed to room temperature for 1.5 h, the reaction mixture was concentrated under reduced pressure. The resulting mixture was taken by $H_2O$ and was then extracted with $CH_2Cl_2$ (3×30 mL). The combined organic layers were dried over anhydrous $Na_2SO_4$. The solvent was removed in vacuo to give a crude product (1.39 g). Recrystallization of crude product from $CH_2Cl_2$/MeOH gave a pure product as a white crystalline (0.71 g, 47% yield). Mp 75.5°–76.5° C.

c) Preparation of [2R,5R-Bis(diphenylphosphino)hexane]ruthenium (II) Acetate Complex Dichloro-(1,5-cyclooctadiene)ruthenium polymer (84 mg, 0.30 mmol) and 2R,5R-bis(diphenylphosphino)hexane (154 mg, 0.34 mmol) were charged into a round-bottom flask in a dry-box. To this were added degassed toluene (20 mL) and triethylamine (0.5 mL, 3.56 mmol). The resulting brown suspension was refluxed under argon stream for 7.5 h. The reaction mixture was cooled to room temperature and the solvent was removed under vacuum to give a brown solid. Anhydrous sodium acetate (255 mg, 3.11 mmol) and degassed tert-butanol (15 mL) were added. The mixture was refluxed under argon stream overnight (14 h). The reaction mixture was cooled to room temperature and the solvent was removed in vacuum. The resulting brown solid was extracted with degassed Et$_2$O (3×7 mL) and combined extracts were evaporated in vacuum. The brown residue was again extracted with degassed EtOH (3×7 mL) and combined extracts were evaporated in vacuum. The resulting solid was extracted with Et$_2$O (5 mL) and degassed tert-butanol (5 mL). The combined extracts were evaporated in vacuum to give a brown solid (222 mg, 97% yield). MP: 125°–127° C. (decomp).

EXAMPLE 2

Hydrogenation of 2-(4-Isobutylphenyl)propenoic Acid (UA)

[2R,5R-Bis(diphenylphosphino)hexane]ruthenium-(II) acetate (18 mg, 0.027 mmol), UA (282 mg, 1.38 mmol), and degassed methanol (15 mL) were charged into a 25-mL flask in a glove-box. The mixture and methanol-washing (15 mL) were transferred to the 100 mL Monel Parr Reactor in a glove-box. The autoclave was purged with H$_2$ (4×300 psi) and was then pressurized with H$_2$ to 1000 psi. The mixture was stirred at 23° C. for 19 h. A small aliquote was removed and GC analysis showed 100% conversion. HPLC analysis showed 27% enantiomeric excess of S-(+)-ibuprofen.

I claim:

1. A ruthenium phosphine complex having the formula

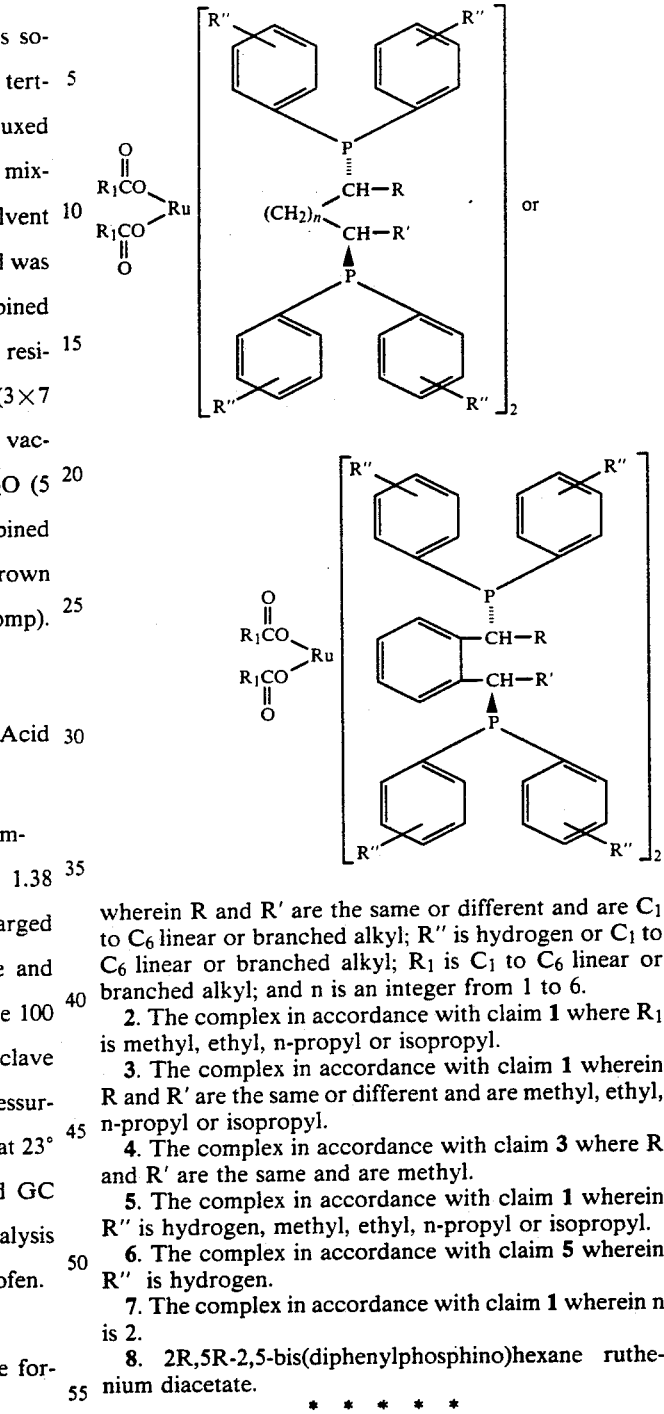

wherein R and R' are the same or different and are $C_1$ to $C_6$ linear or branched alkyl; R" is hydrogen or $C_1$ to $C_6$ linear or branched alkyl; $R_1$ is $C_1$ to $C_6$ linear or branched alkyl; and n is an integer from 1 to 6.

2. The complex in accordance with claim 1 where $R_1$ is methyl, ethyl, n-propyl or isopropyl.

3. The complex in accordance with claim 1 wherein R and R' are the same or different and are methyl, ethyl, n-propyl or isopropyl.

4. The complex in accordance with claim 3 where R and R' are the same and are methyl.

5. The complex in accordance with claim 1 wherein R" is hydrogen, methyl, ethyl, n-propyl or isopropyl.

6. The complex in accordance with claim 5 wherein R" is hydrogen.

7. The complex in accordance with claim 1 wherein n is 2.

8. 2R,5R-2,5-bis(diphenylphosphino)hexane ruthenium diacetate.

* * * * *